United States Patent [19]

Kyle

[11] 4,438,762
[45] Mar. 27, 1984

[54] ORTHOPEDIC HIP FIXATION DEVICE

[75] Inventor: Richard F. Kyle, 825 S. 8th St., Ste. 302, Minneapolis, Minn. 55404

[73] Assignee: Richard F. Kyle, Minneapolis, Minn.

[21] Appl. No.: 335,808

[22] Filed: Dec. 30, 1981

[51] Int. Cl.³ .............................................. A61F 5/04
[52] U.S. Cl. .............................. 128/92 BB; 128/92 B; 128/92 CA
[58] Field of Search ............ 128/92 B, 92 BA, 92 BB, 128/92 EB

[56] References Cited

U.S. PATENT DOCUMENTS

| | | | |
|---|---|---|---|
| 2,526,959 | 10/1950 | Lorenzo | 128/92 BB |
| 3,727,611 | 4/1973 | Schultz | 128/92 EB |
| 3,782,374 | 1/1974 | Fischer | 128/92 BB |

FOREIGN PATENT DOCUMENTS

| | | | |
|---|---|---|---|
| 2030249 | 12/1971 | Fed. Rep. of Germany | 128/92 BB |
| 2127881 | 12/1971 | Fed. Rep. of Germany | 128/92 BB |

Primary Examiner—Richard J. Apley
Assistant Examiner—David J. Isabella
Attorney, Agent, or Firm—Hubbard & Stetina

[57] ABSTRACT

An apparatus useful in reduction of fractures in the vicinity of the neck of the femur comprising a lag screw for being threadably received in or adjacent the head of the femur, and extending through the neck of the femur, an annular sleeve telescopingly receiving the shaft of the lag screw, with means capturing the lag screw within the sleeve for limited telescoping movement therein, and a trochanteric plate for securement to adjacent cortex portions of the femur is disclosed.

1 Claim, 5 Drawing Figures

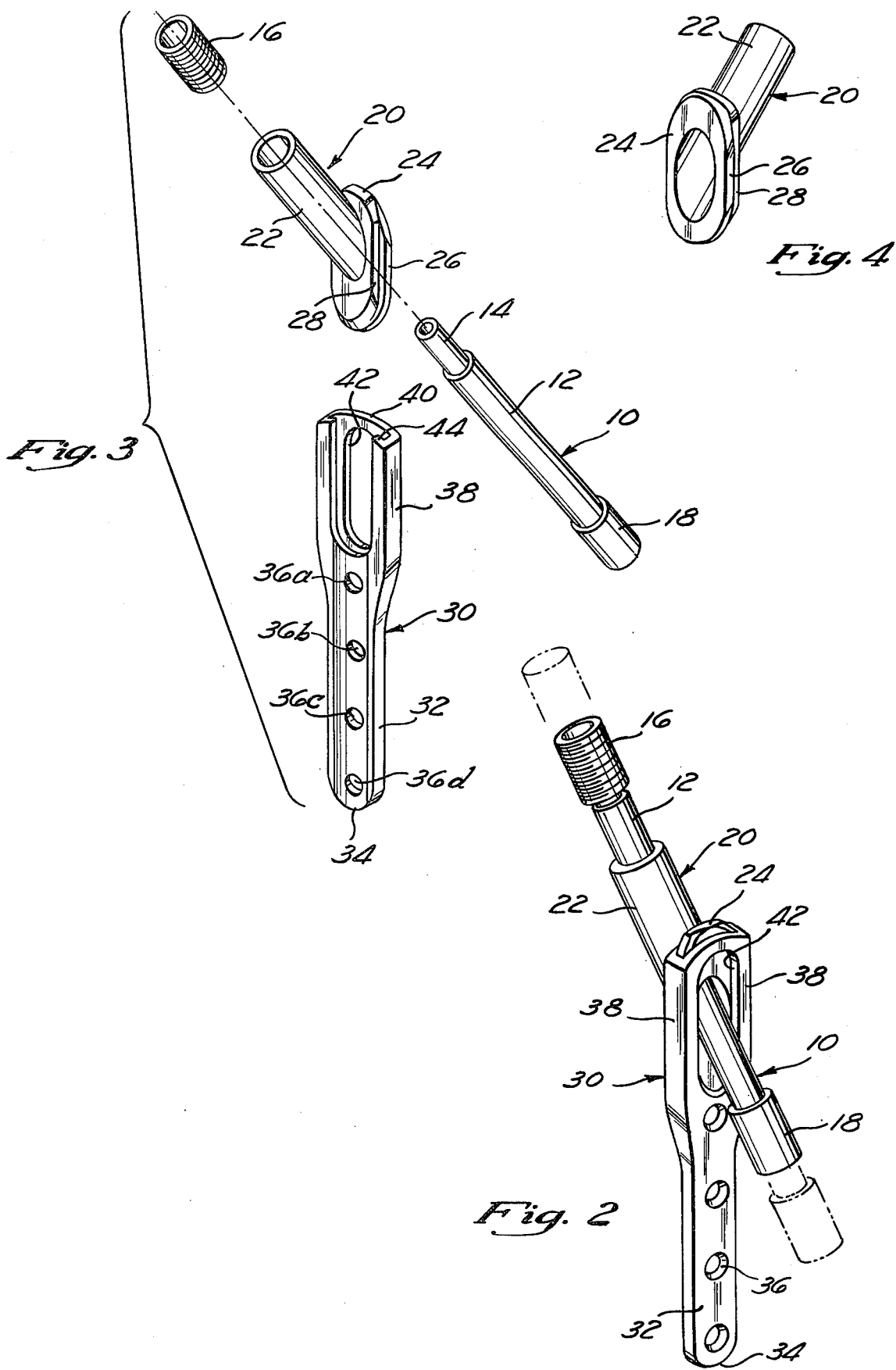

ORTHOPEDIC HIP FIXATION DEVICE

TECHNICAL FIELD

This invention relates to orthopedic appliances and, more particularly, to appliances used in the reduction of hip fractures in which the neck of the femur is the site of the fracture.

BACKGROUND OF THE INVENTION

Hip fractures, wherein the femur is fractured one or more times in the area of the femur or immediately subjacent the head, are comparatively common. A great many devices have been proposed for the reduction of fractures of this type. While many of these devices have found the application and have advantages relative one to another, there remain some problems and areas of continuing concern.

Such reduction devices consist, basically, of an elongate lag screw which is threaded on one end to be threadably received in the head of the femur, and is secured to a plate such that when the lag screw is tightened, the head of the femur is forceably compressed at the fracture line to the remainder of the femur. Devices of this type, generally, are described in the U.S. Pat. Nos. 2,526,959 and 3,554,193, in which various modifications in the manner of attachment of the lag screw to the trochanteric plate have devised.

It has also been recognized that various adjustment features are important in treating certain femural fractures. In general, fastener devices with such adjustment features employ a guide sleeve which is imbedded in one bone segment, such as the upper segment of the femur, in order to receive and adjustably hold one end of an axially elongated shaft, e.g. a lag screw, which extends through both fractured bone segments, with the end of the shaft opposite the guide sleeve being provided with structure for securing the shaft to the head of the femur. Because of absorption occurring during the healing process, it has been necessary, in some instances, to accommodate a certain amount of telescoping movement between the shaft and the guide sleeve. Clasping devices within this class generally are described in the U.S. Pat. Nos. 3,996,931 and 4,095,591, both of which also refer to other patents which have related disclosures.

Functionally, some of these devices perform quite satisfactorily for many fractures of the femur but are extremely difficult for the surgeon to properly implant. It is, therefore, of great importance to provide a fixation device which is not only functional in providing the necessary stability and guidance in the reduction of the fracture, but can be efficiently, accurately and quickly implanted by the surgeon. A principal feature of the invention is to provide a device which accomplishes the desired heretofore achieved result.

STATEMENT OF THE INVENTION

The present invention features a lag screw adapted to be affixed into or adjacent the head of the femur and which extends, when in use, through the neck of the femur, which is telescopically and captively received in a guide sleeve which, in turn, is received in alignment with the lag screw in the trochanteric area of the femur. The guide sleeve means slidably receives the lag screw and is affixed to the trochanteric plate at a predetermined angle relative to the femur axis. The inventive device can be quickly and efficiently implanted without concern for assuring independently the alignment of the lag screw in the femur head and in the guide sleeve. The guide sleeve is permanently but telescopically fitted around the shaft of the lag screw, thus assuring proper alignment. The guide sleeve can then be easily fitted into the trochanteric plate and the plate then affixed to the femur using conventional screws.

BRIEF DESCRIPTION OF THE DRAWINGS

FIG. 2 is a perspective view of the device of this invention showing the relationship of and the telescopic ability of the lag screw of the device.

FIG. 3 is an exploded view of the elements of the present invention.

FIG. 4 is a perspective view of the guide sleeve.

DESCRIPTION OF THE BEST MODE

Figure 1:
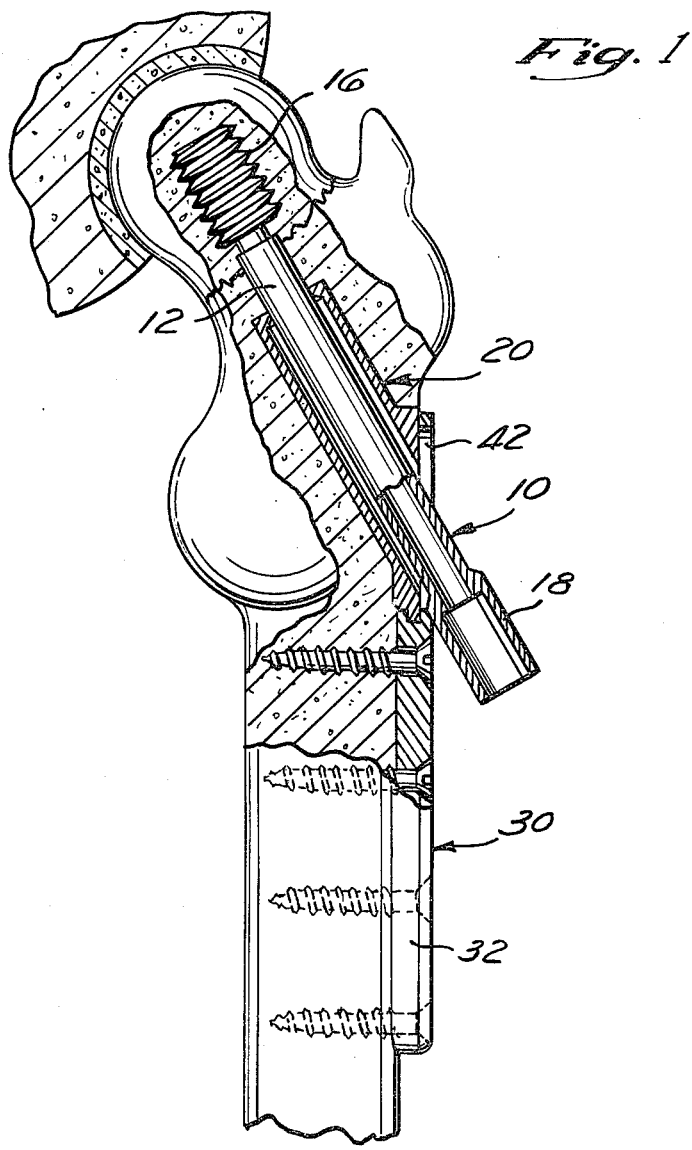
FIG. 1 is an anterior view of the upper portion of the femur showing the device of this invention fitted, as it would be in use, with portions of the femur being cut away for illustrative purposes.

The present invention comprises a specific relationship described hereinafter, three distinct assemblies which may be manufactured unitarily, by machining or milling, or may be made in a number of components and welded or pressed or otherwise secured together.

The first major element is the lag screw 10. The lag screw 10, comprises a shaft 12, and in the preferred embodiment, comprises an extension 14, adapted to be press fitted, welded, or otherwise affixed into a threaded distal end piece 16, which is adapted to be threaded into the femur. The lag screw 10, is telescopically received for slidable movement along the axis of the lag screw within the guide sleeve 20, which will be described in detail. Importantly to this invention, means such as keeper 18, is provided on or in association with the lag screw, or unitarily formed therewith, to capture the lag screw in its telescopic, slidable relation in the sleeve, such that it cannot be removed and must always remain received in the sleeve and, of course, in axial alignment with the sleeve.

The sleeve 20 comprises a hollow cylindrical portion 22, to which a head 24 is secured or formed. The head 24 comprises an extending flange 26, adapted to be received in a slot in the trochanteric plate. The juncture of the flange with the head forms a shoulder 28, which coacts with the trochanteric plate to assist in fixing a predetermined angle between the trochanteric plate and the lag screw.

The trochanteric plate 30 comprises an attachment portion 32 which extends, in usage, down the femur, and which is preferably provided with a generally cylindrical inner configuration to permit it to fit tightly upon the femur, as indicated in 34, and a number of holes 36 through which convention bone tapping screws may be inserted to attach the trochanteric plate through the cortex of the femur. The trochanteric plate also comprises an enlarged sleeve receiving portion indicated generally at 38, which comprises a central web portion 40, through which an elongate aperture 42, is formed. On the respective signs of the aperture 42, and displaced from the web 40, there is a flange which extends on two sides of the aperture and includes portions of the flange which extend toward each other, spaced below the web. This space forms a slot for receiving the flange 26 of the sleeve, the shoulders 28 being slidably engaged with flange 44.

The assembly of the device of this invention can best be understood by reference to FIGS. 2 and 3. As shown in FIG. 3, the trochanteric plate is slidably removable from the sleeve. It can be easily received upon the sleeve. The assembly is shown in FIG. 2.

Figure 5:
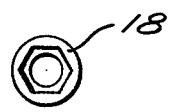
FIG. 5 is an end view of the proximal end of the lag screw, showing the means therein for permitting the lag screw to be threaded into the head of the femur.

In use, the surgeon, using conventional bone taps and drills, forms a passage through the neck of the femur into or immediately subjacent the head of the femur and, depending upon the thread structure of the lag screw, into the head of the femur if necessary. In forming this passage, the surgeon must make certain that the femur neck and head fragments are in proper position relative to each other however, as will be seen, some small margin of error is permitted in this alignment. Next, the surgeon inserts the sleeve and lag screw assembly, the lag screw being permanently captured in the sleeve, into the passage and, using an appropriate tool, taps the head of the screw into the head of the femur, or into the neck of the femur immediately subjacent the head. As illustrated in FIG. 5, an Allen Head or other engaging means is provided to permit the lag screw to be turned by a mating tool. An Allen socket for receiving an Allen wrench is a quite satisfactory arrangement, but any other means to permit twisting of the lag screw will be equally satisfactory.

Since the sleeve always carries the lag screw in captive telescopic relationship, the alignment of the sleeve and the lag screw is maintained. Thus, when the surgeon affixes the threaded distal end of the lag screw into the head of the femur, the head of the femur is fixed in alignment with the guide sleeve. This permits the head of the femur, that fragment which has been broken off at the fracture line, to telescope relative to the remainder of the femur, to accommodate for changes during bone growth and heating while yet maintaining the proper alignment between the femur and the femur head.

Significantly, this operation can be accomplished with much greater ease and very much more quickly than can be done with devices with which the inventor is familiar or aware. The fixing of the threaded distal end of the lag screw into the head of the femur, while the lag screw is telescopically received in alignment in the guide sleeve and is maintained there by a keeper 14 or other means which maintains the captive relationship, greatly simplifies the entire operation. Moreover, this arrangement reduces the difficulties in trying to bring the sleeve into alignment with the lag screw and also with the passageway through the trochanteric plate area of the femur.

INDUSTRIAL APPLICATION

The present invention finds use in orthopedic surgery generally and, most particularly, in the reduction of hip fractures.

What is claimed is:

1. A femur fracture reduction device, comprising:
   an elongate shaft having a distal end and a proximal end;
   a keeper connected to the proximal end of the shaft;
   a guide sleeve including a cylindrical portion having a passage therethrough for slidably receiving the elongate shaft therein;
   a flanged head mounted to an end of the guide sleeve;
   a threaded end portion mounted on the distal end of the elongate shaft, the threaded end portion and the keeper cooperating to retain the elongate shaft inside the passage in the guide sleeve, the threaded end portion being formed for threadedly engaging the head of a patient's femur; and
   a trochanteric plate including means for permitting attachment of the plate to the femur and a slot for slidably receiving the guide sleeve head at a predetermined angle with respect to the trochanteric plate, such that during use, the assembled guide sleeve and the elongate shaft with the threaded end portion mounted thereon are fitted into an aperture in the patient's femur with the threaded end portion being threadedly affixed to the head of the femur to retain the head of the femur in alignment with the neck of the femur to reduce a fracture thereof and the elongate shaft being telescopically slidable within the guide sleeve to accommodate changes which may occur during healing of the fracture.

* * * * *